(12) United States Patent  (10) Patent No.: US 7,401,720 B1
Durrani  (45) Date of Patent: Jul. 22, 2008

(54) DUAL SURGICAL STAPLER

(76) Inventor: Ayaz Mahmud Durrani, 7777 SW. Freeway, Suite 1068, Houston, TX (US) 77074

( * ) Notice: Subject to any disclaimer, the term of this patent is extended or adjusted under 35 U.S.C. 154(b) by 275 days.

(21) Appl. No.: 11/429,781

(22) Filed: May 8, 2006

Related U.S. Application Data

(63) Continuation-in-part of application No. 10/840,997, filed on May 7, 2004, now abandoned.

(51) Int. Cl.
*A61B 17/068* (2006.01)

(52) U.S. Cl. .................. 227/176.1; 227/19; 227/109; 227/175.1; 606/153; 606/219

(58) Field of Classification Search ............. 227/175.1, 227/19, 109, 176.1, 83, 88; 606/153, 139, 606/219, 216
See application file for complete search history.

(56) References Cited

U.S. PATENT DOCUMENTS

| 2,881,762 | A |   | 4/1959  | Lowrie |  |
|---|---|---|---|---|---|
| 4,534,350 | A |   | 8/1985  | Goldern |  |
| 4,595,007 | A |   | 6/1986  | Mericle |  |
| 4,617,928 | A | * | 10/1986 | Alfranca ................... 227/180.1 |
| 4,979,954 | A | * | 12/1990 | Gwathmey et al. .......... 606/219 |
| 5,163,598 | A | * | 11/1992 | Peters et al. ............. 227/176.1 |
| 5,540,374 | A | * | 7/1996  | Klinzing et al. .......... 227/176.1 |
| 5,738,474 | A |   | 4/1998  | Blewett |
| 5,833,698 | A | * | 11/1998 | Hinchliffe et al. ............ 606/153 |
| 5,862,972 | A | * | 1/1999  | Green et al. ............. 227/175.1 |
| 6,024,748 | A | * | 2/2000  | Manzo et al. ............... 606/153 |
| 6,638,297 | B1 |  | 10/2003 | Huitema |
| 7,223,273 | B2 | * | 5/2007  | Manzo ....................... 606/153 |

\* cited by examiner

*Primary Examiner*—Scott A. Smith
(74) *Attorney, Agent, or Firm*—Buskop Law Group, PC; Wendy Buskop

(57) ABSTRACT

A dual staple disposable surgical gun, wherein the gun fires two staples in a staggered formation simultaneously to close an incision in the skin to prevent the skin overlapping. The dual staple disposable surgical gun comprises a frame structure, adapted to be held by a hand with a grip having a handle. A first staple track and a second staple track each with an advancing blade and a spring mechanism is incorporated to aid in the injection of the staples. A translatable driver manually actuates both staple tracks to eject a single pair of staples simultaneously when the dual staple disposable surgical gun is squeezed. The dual staple disposable surgical gun additionally includes a biasing means for returning the translatable driver from a staple ejecting position to a staple reloading position.

12 Claims, 9 Drawing Sheets

DUAL SURGICAL STAPLER

CROSS REFERENCE TO RELATED APPLICATIONS

The present application is a Continuation-in-Part to U.S. patent application Ser. No. 10/840,997 filed on May 7, 2004, now abandoned.

FIELD

The present embodiments pertain to a disposable dual surgical stapler gun and more specifically, a dual surgical stapler gun and a method for the use of a dual surgical stapler gun as a tissue fixation device.

BACKGROUND

In normal surgery, simple sutures using thread have often been used.

A simple suture involves using a plurality of simple stitches each with a knot to hold the skin together. There are situations when these simple sutures are unsatisfactory because the skin overlaps during healing causing scarring. Surgical situations exist wherein sutures with a needle and thread simply take too long. For example, situations when the patient should not be kept under anesthesia any longer than necessary would require a quick method of closure. Extended time under anesthesia increases the patient's risk of complications.

To provide a fast method to hold skin together, staples were developed having one of three basic shapes, a C-shape, a U-shape and a circular shaped member. These simple staples have advantages over the simple sutures for quickness in implementation, but has a negative effect in that the skin usually overlaps during healing. Overlapping skin can cause scarring or a ridge to form. This ridge or scar can delay the healing process as well as be a cosmetically undesirable feature. Also with overlapping skin, the healing process is prolonged.

As an alternative to simple suturing, mattress suturing was developed. The mattress suture prevents overlapping of the edges of the incision and improved the healing process by quickening the healing process of the skin and reducing the incidence of unsightly scarring of the skin.

The mattress suture, regrettably takes an even longer time to implement than the simple suture. The mattress suture causes the wound to heal faster and reduces scarring but requires more anesthesia time for the patient, which is can have negative effects. This mattress type of suturing involves placing on each edge of the incision, a stitch immediately near the edge of an incision or wound and then making a second stitch further from the edge of the incision or wound to approximate the two edges of the incision or wound and reduce tension on the wound while preventing an overlap of the edges of the incision.

The present embodiments were designed to provide the advantages of the mattress suturing technique with the improved quality of a dual staple system.

The predominant form of staple includes a central portion, either straight or slightly curved, with bilateral opposing side portions that are sharply beveled so as to penetrate the skin easily. This form of staple is generally applied utilizing a stapling apparatus that forcefully drives the opposing beveled side portions through the tissue margins in a ninety degree arc so that these beveled opposing side portions are generally facing one another at the completion of the stapling operation. The bending of the opposing beveled side portions form generally parallel planes into a generally horizontal plane is often accomplished utilizing a ram and opposing ram plate that cooperatively forcefully bend the opposing beveled side portions during a stapling operation.

Another conventional surgical staple includes a generally U-shaped fastening member having legs that are received in two bores of a receiver member. This type of surgical staple is limited by the need to grasp the members both above and below the tissue plane.

A third surgical staple involves an open circular-shaped member, which when closed, has the free ends laterally disposed with respect to each other forming a split-ring configuration.

A need exists to prevent the overlap of the skin when drawing the edges of the skin together. A need exists for a disposable dual surgical stapler gun that is fast to use and will help keep the edges of the skin together for an extended time without an overlap. A need exists during the healing period after surgery for a secure stapling system that holds the skin together without an overlap to insure better healing and less scarring of the skin.

The present embodiments have been developed to meet these needs.

SUMMARY

The present embodiments relate to a dual staple disposable surgical stapler gun, wherein the gun fires two staples simultaneously to close an incision in the skin without the skin overlapping. The stapler simultaneously fires two staples in a staggered formation to give a closer and stronger approximation of the edges of the incision.

The dual staple disposable surgical stapler gun consists of a frame structure adapted to be held by a hand with a grip having a handle. The first staple track is disposed on top of the second staple track in a staggered relationship, each staple track being adapted for holding staples. The first staple track and the second staple track each have an advancing blade and a spring mechanism.

A translatable driver manually actuates both staple tracks to eject a single pair of staples simultaneously by the hand. The pair of staggered staples eject simultaneously for engagement on both sides of the incision forming a mattress suture. The first staple engages a first arm close to a first edge of the incision and a second arm a distance from the second edge of the incision and the second staple engages a first arm close to a second edge of the wound and the second arm engages a distance from the first edge of the wound to achieve dual staple mattress suturing.

There includes a biasing means for returning the translatable driver from a staple ejecting position to a staple reloading position. The translatable driver having a force transmission member linking together the translatable driver and a connecting end portion engageable with a spring connected to the translatable trigger portion.

BRIEF DESCRIPTION OF THE DRAWINGS

The present embodiments will be explained in greater detail with reference to the appended Figures, in which.

Figure 1:
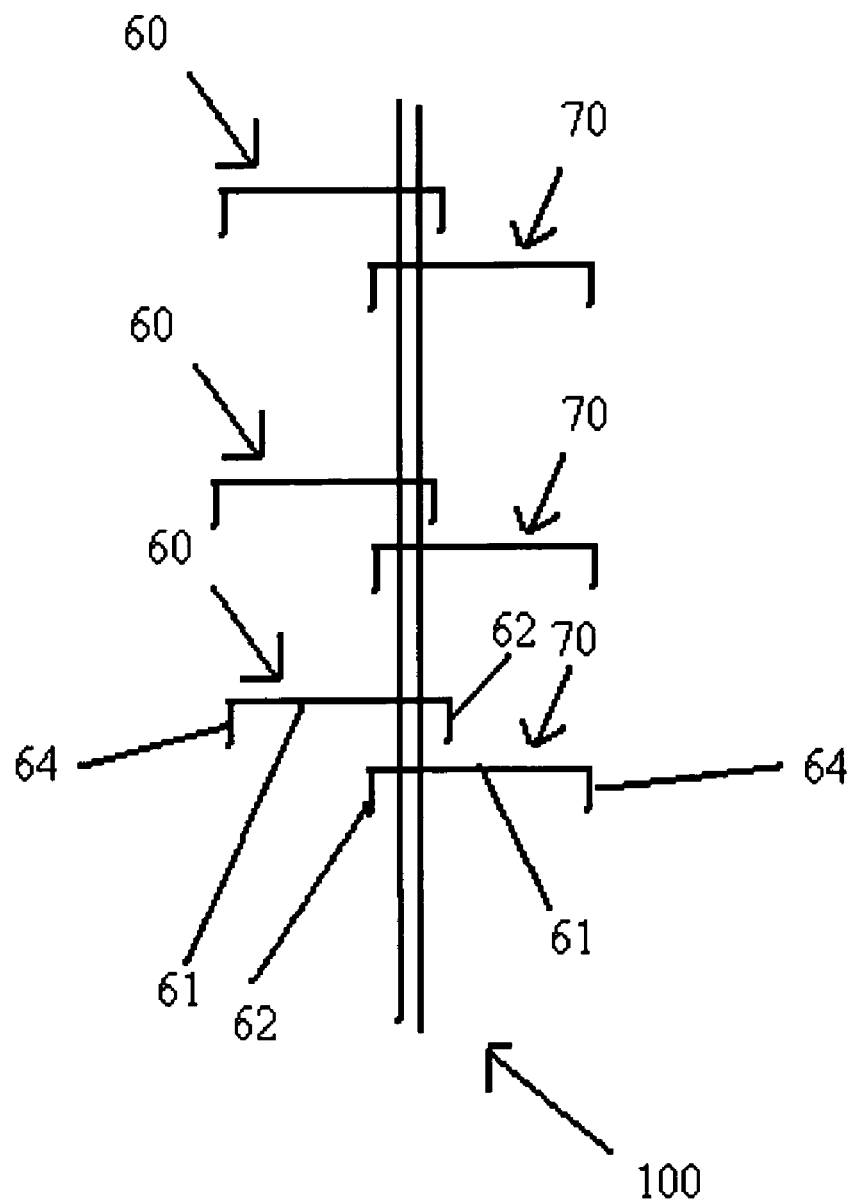
FIG. 1 depicts a dual staple system.

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments herein and can be practiced or carried out in various ways.

Embodied devices herein are for a disposable dual surgical stapler gun that simultaneously propels two surgical staples in a staggered fashion for closing incisions in skin. In general, the surgical staples have a body portion constructed from a rod and have a planar structure. The body portion consists of a crown with leg projections from each end. Each leg comprises a skin piercing projection to assist in the staple being inserted into the skin.

In a pre-stressed situation, the widths for a surgical staple to be used with humans are typically between 2.5 mm and 3.5 mm and the second widths are typically between 1.5 mm and 2.5 mm. For humans, the most preferred width contemplated is, for the first width, 3 mm and for the second width is 2 mm.

If the surgical staple is designed for use with large animals, such as a horse or cow, giraffe or other large zoo animal, the first width is typically 7.5 mm to 10.5 mm and the second width is typically between 3 mm and 7.5 mm. The preferred width for large animals is typically 9 mm for the first width and 6 mm for the second width.

The skin piercing projections are adapted to accept stress, such as from a surgical stapler. An example of a surgical stapler is the Ethicon Proximate RH 35W that is used to implant the surgical staple in the skin of a human or an animal. The surgical stapler is used to embed the staple operated manually and transform the generally planar structure of the body of the surgical staple to a stressed position.

In the stressed position, where the piercing projections are disposed on skin on opposite sides of a wound. The piercing projections are then bent by the staple into essentially the same plane holding the skin together in a position tantamount to that of a mattress suture.

Upon cessation of the application of stress, the surgical staple maintains the stressed position enabling the surgical staple to draw opposite margins of skin toward each other in a non-overlapping manner. When the skin piercing projections are bent, the two projections or arms are in an angular relation to each other at 180 degrees, but variations from this angle would still work, if the variation is no more than 20 degrees.

In an embodiment, the surgical staple is made from a rod of a lightweight, non-rusting alloy, such as stainless steel.

In another embodiment, the surgical staple is adaptable for human use and small non-human animals. A small non-human animal that this staple would work on could be a dog, a cat, a raccoon, a chicken, or similar creatures. For such "small animal" use, the pre-stressed staple preferably has a height between 4 mm and 6 mm, a length between 2 cm and 3 cm, and a diameter of the rod from between 0.5 mm to 0.8 mm.

Alternatively, the novel surgical staple can be for large non-human animals, like giraffes, elephants, other zoo animals, horses, cows, large birds, dolphins, or similar large animals with a skin or skin like covering. In this larger embodiment, the surgical staple comprises a height between 12 mm to 18 mm, a length between 6 cm and 9 cm, and a diameter of the rod between 1.5 mm and 2.4 mm.

The body of the staple is can be a solid rod structure, but the body can be a hollow bendable rod as well.

With reference to the figures, FIG. 1 depicts an embodiment of a dual staple system embedded in skin closing an incision (100). The dual surgical staple system includes two staples, a first staple (60) and a second staple (70), per staple location. Each staple (60 and 70) includes a crown (61) with two ends. Each staple includes a first arm (62) and a second arm (64) attached at each end of the crown (61). The arms extend from the crown in a direction substantially perpendicular to the crown when the staple is in an unstressed position.

As a method, the two staples are loaded into a surgical stapler. The surgical stapler is located over an incision in the skin that needs to be closed. The stapler is activated and the arms of each stapler are inserted into the skin.

Figure 2:
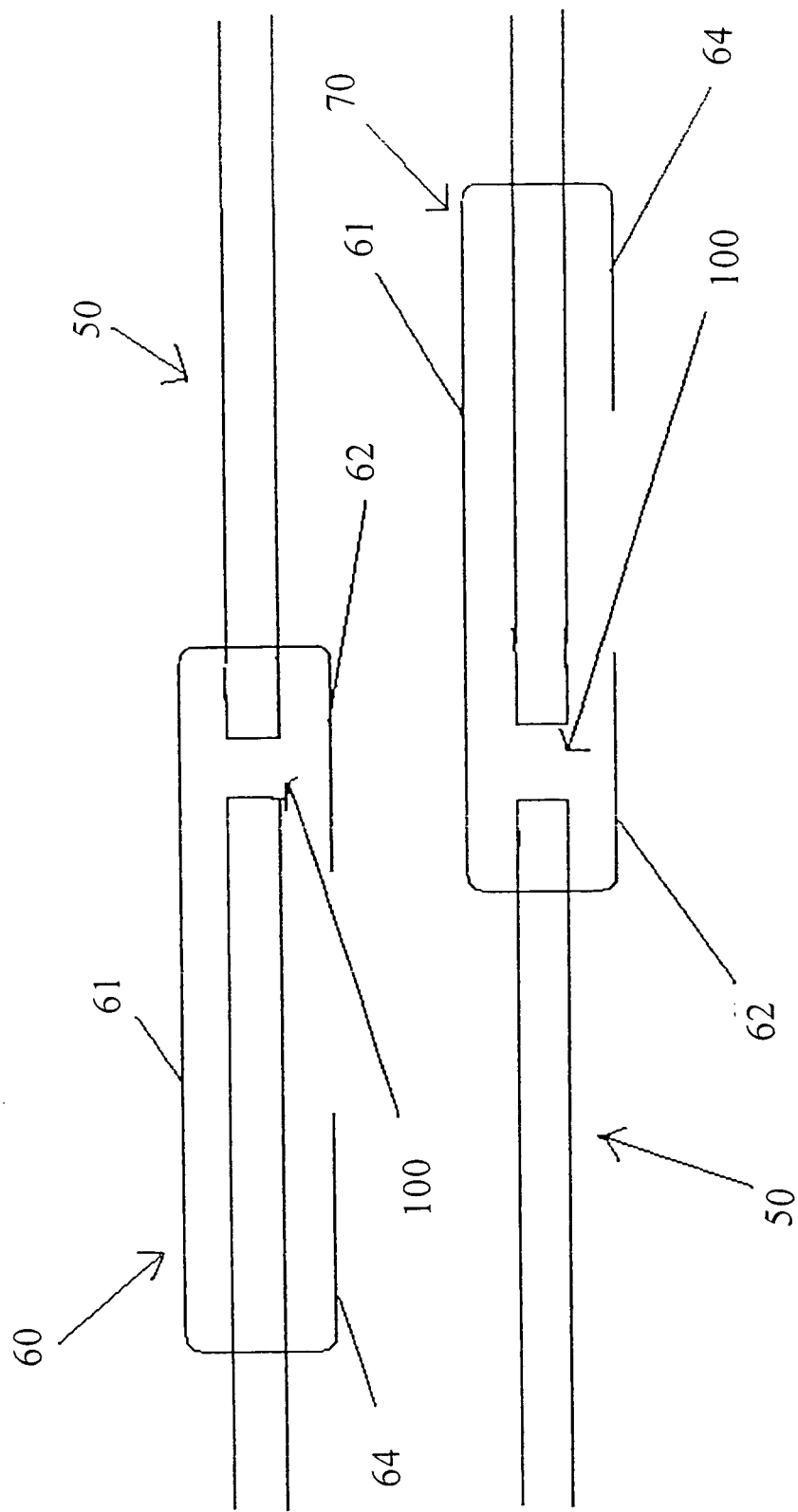
FIG. 2 depicts insertion of the dual staples around an incision.

As depicted in FIG. 2, the first arm (62) is inserted in the skin (50) near the incision (100) and is bent towards the incision (100). Typically, the first arm (62) intersects the incision in order to ensure that the two sides of the skin are held together. In one embodiment, the first arm (62) is bent so that the bended end is close to the surface of the skin, as depicted in FIG. 2. The dual staples, when bent into the skin around the incision, generally can form a rectangular shape or an inverted G-shape with a gap.

The second arm (64) is inserted in the skin (50) away from the incision (100) and is bent towards the incision (100) in order to secure stabilization of the union of the two edges of skin.

The disposable dual surgical staple gun causes no skin overlap, promotes faster healing of the skin, and it is faster to close the skin incision with staples which reduces the need for anesthesia time for the patient, which can be a lifesaving step. Often prolonged exposure to anesthesia cannot be tolerated by sick patients.

In another embodiment, each arm has skin piercing projections in order to insert into the skin easier. The skin piercing projections can be either a pointer projection, a chiseled projection, a skewed projection, or combinations of these projections.

In an embodiment of the invention, the staple of the disposable dual surgical staple gun uses skin piercing projections with pointed ends that resemble a chisel-like structure. Medical needles use a "beveled" or chisel-like structure to provide a means to invade the skin with maximum ease and minimal pain. In another embodiment, each of the skin piercing projections can have a beveled end.

In another embodiment of the surgical staple, the pre-stressed surgical staple is placed upon the skin, and then the staple is stressed, drawing the skin piercing projections slightly together, with the first and second skin piercing projections becoming disposed in a generally horizontal plane relative to the body of the staple.

The mattress staple can be used with all surgical skin incisions. Another embodiment is a method of use for applying a mattress staple that is usable in adults, children, or even non-human animals, such as thoroughbred horses.

The present embodiment relates to a dual staple disposable surgical gun, wherein the gun fires two staples in a staggered formation simultaneous to close an incision in the skin without the skin overlapping. The dual staple disposable surgical gun has a frame structure, adapted to be held by a hand with a grip having a handle.

The dual staple disposable surgical gun has a first staple track and a second staple track each with an advancing blade and a spring mechanism. The first staple track is disposed on top of the second staple track in a staggered relationship, each staple track being adapted for holding staples. A translatable driver is positioned on the dual staple disposable surgical gun for manually actuating both staple tracks to eject a single pair of staples simultaneously by the hand. The pair of staggered staples eject simultaneously for engagement on either side of the incision forming a mattress suture and wherein the first staple engages a first arm close to a first edge of the incision and a second arm a distance from a second edge of the incision and the second staple engages a first arm close to a second edge of the wound and the second arm engages a distance from the first edge of the incision to achieve dual staple mattress suturing. The dual staple disposable surgical gun additionally includes a biasing means for returning the translatable driver from a staple ejecting position to a staple reloading position. The translatable driver having a force transmission member linking together the translatable driver and a connecting end portion engageable with a spring connected to the translatable trigger portion.

In an alternate embodiment the dual staple disposable surgical gun can consist of a frame structure comprising a first staple track portion inserted into a second holder portion.

In another embodiment of the dual staple disposable surgical gun the first and second staple tracks each comprise a back and a top and the first and second staple tracks are connected back to back.

In yet another embodiment the dual staple disposable surgical gun fires at least two staples simultaneously each time it is fired. After firing the two staples are staggered in a position from each other across the incision.

In yet another embodiment dual staple disposable surgical gun comprises the gun using staples that have a skin piercing projection comprising of a point projection, a chiseled projection, or a skewed projection. The staple can also comprise a lightweight, non-rusting alloy of a metal. Each staple can have:

a. a height ranging from 4 mm to 6 mm;

b. a length ranging from 2 cm to 3 cm; and c. a diameter of the rod ranging from 0.5 mm to 0.8 mm.

In another embodiment dual staple disposable surgical gun can comprise a gun formed from a crystalline polymer, or a metal. Wherein the gun first width ranges from 2.5 mm to 3.5 mm and the second width ranges from 1.5 mm to 2.5 mm.

The present embodiment also comprises a method for surgically stapling an incision using the simultaneous injection of offset twin surgical staples. The steps begin by inserting surgical staples into a dual staple disposable surgical gun. The surgical staples each comprise a crown comprising two ends, a first arm, and a second arm attached at each end of the crown. The arms of the staple comprise a skin piercing projection, wherein the arms extend from the crown in a direction substantially perpendicular to the crown when the staple is in its initial shape. The dual staple disposable surgical gun comprises a gun that fires two staples simultaneous to close an incision in the skin without the skin overlapping.

The next step for surgically stapling the incision comprises placing the dual staple disposable surgical gun over the incision and activating the stapler by squeezing the grip to simultaneously insert a first staple from a first track and a second staple from a second track into the skin. By activating the stapler the first arm of each staple engages the skin nearest the incision on opposite sides of the incision. The crowns of each staple locate adjacent and parallel to one another, and the second arms of each staple to engage the skin away from the incision on opposite sides of the incision The dual staple disposable surgical gun then bends each arm on the staples forming an inverted G-shape with a gap.

In another embodiment the step of using the dual staple disposable surgical gun bends each arm to ensure that the first arms intersects the incision.

In yet another embodiment the step of using the dual staple disposable surgical gun bends each arm thereby closing the incision in the skin without the skin overlapping.

Figure 3:
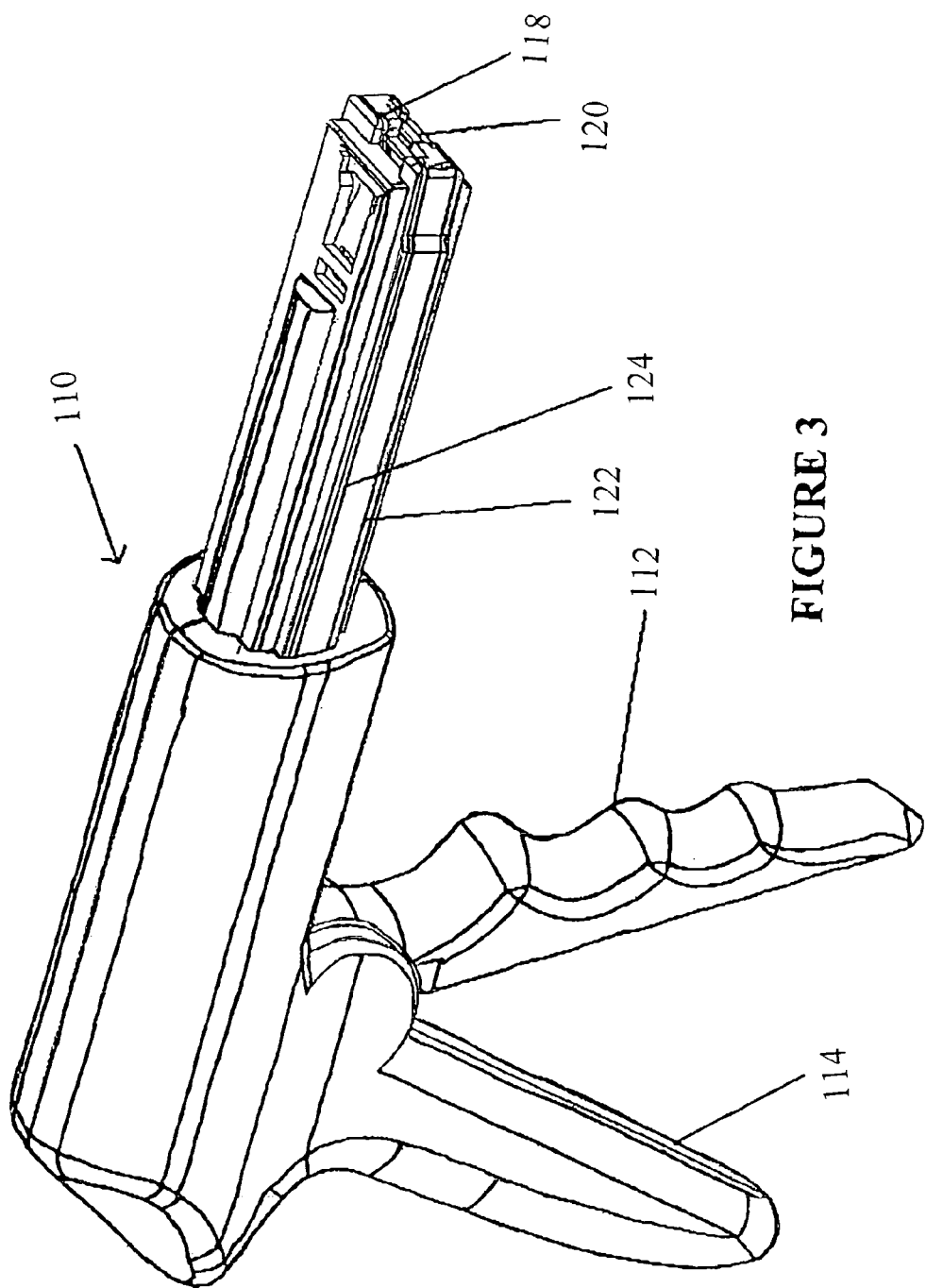
FIG. 3 depicts a perspective view of a dual stapler gun.

FIG. 3 depicts a perspective view of the dual stapler gun. The dual staple disposable surgical gun (110) comprises a grip (112) having a handle (114). A first staple track (118) and a second staple track (120) are located on the dual staple disposable surgical gun. The staple tracks extend throughout the dual staple disposable surgical gun as shown through the first staple track portion (122) and the second staple track portion (124).

Figure 4:
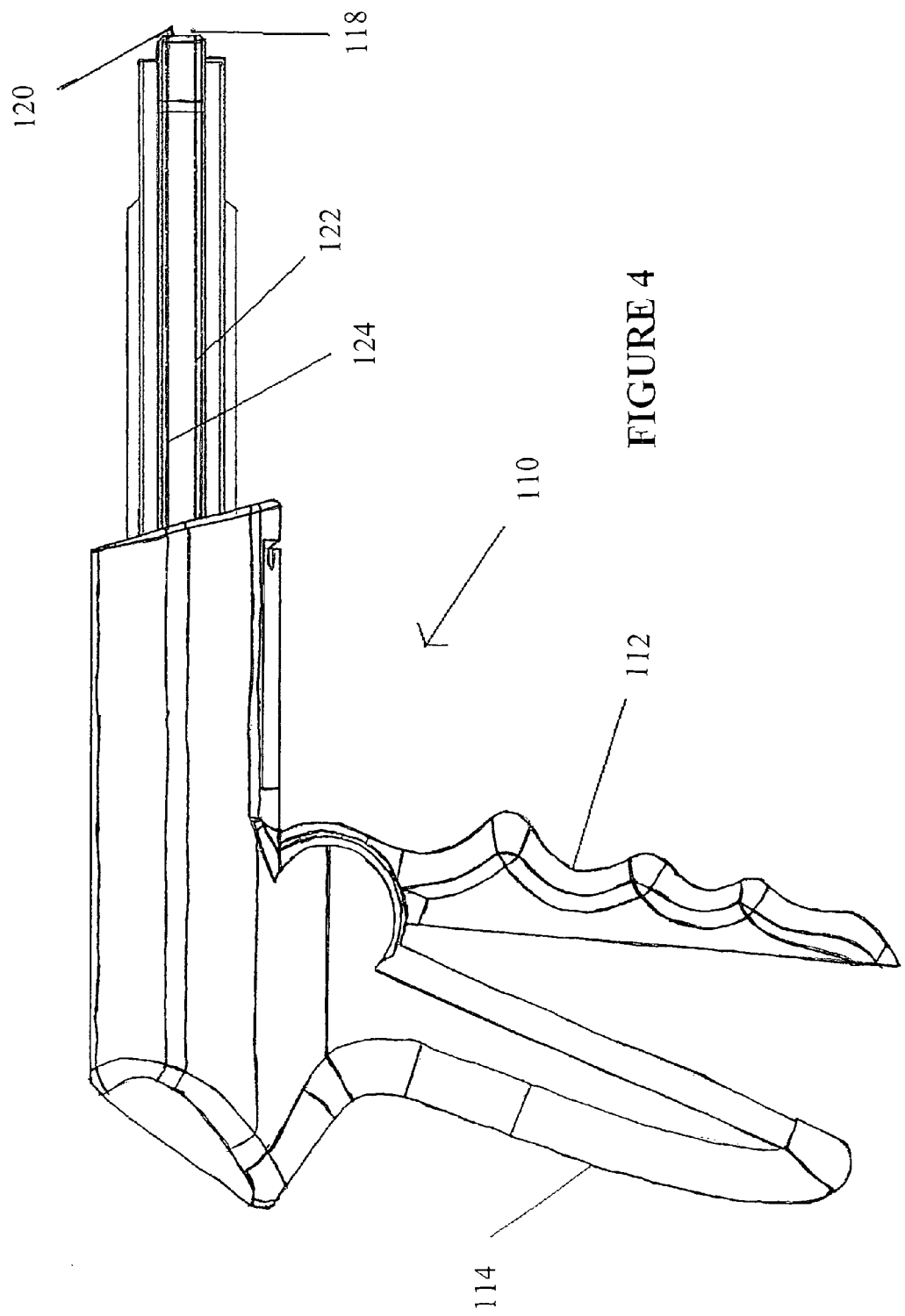
FIG. 4 depicts a side view of the dual stapler gun.

FIG. 4 depicts a side view of the dual stapler gun with the grip compressed. When the grip is compressed staples are ejected from the holes in the front of the stapler.

Figure 5:
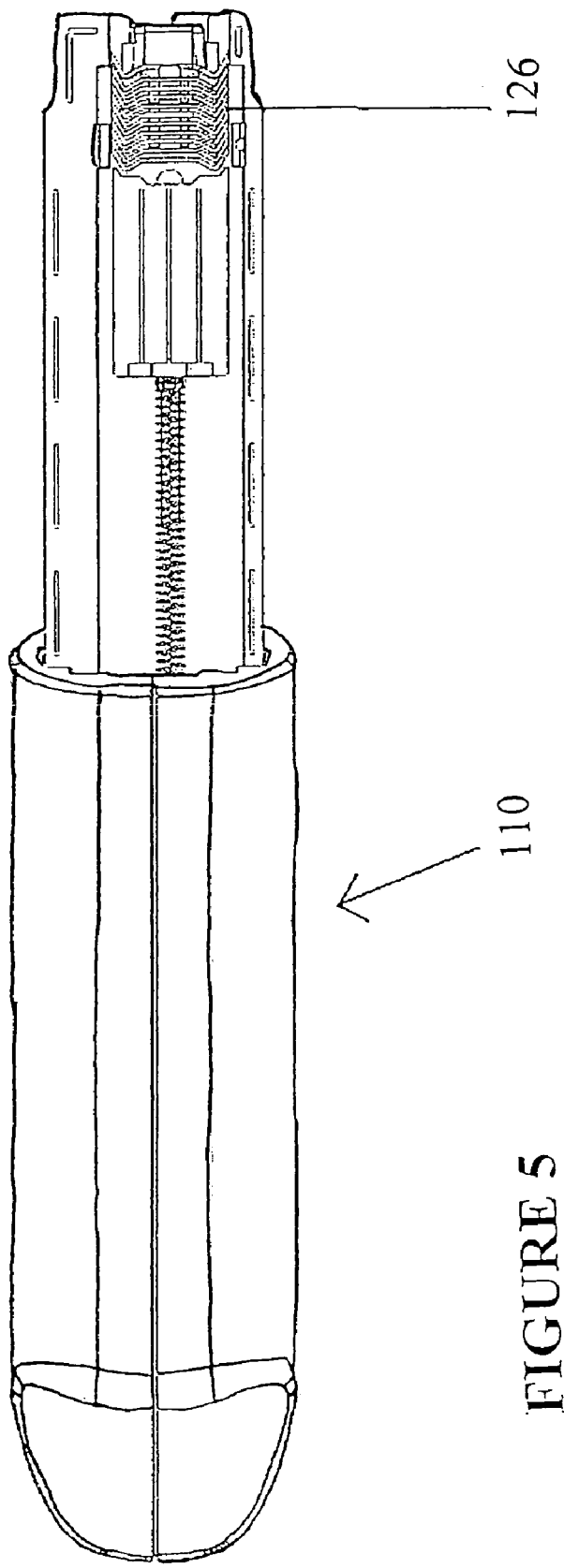
FIG. 5 depicts a top view of the dual stapler gun.

FIG. 5 depicts a top view of the dual stapler gun. From the top view of the staple track staples (126) can be shown lined up ready to be manually actuated by the translatable driver.

Figure 6:
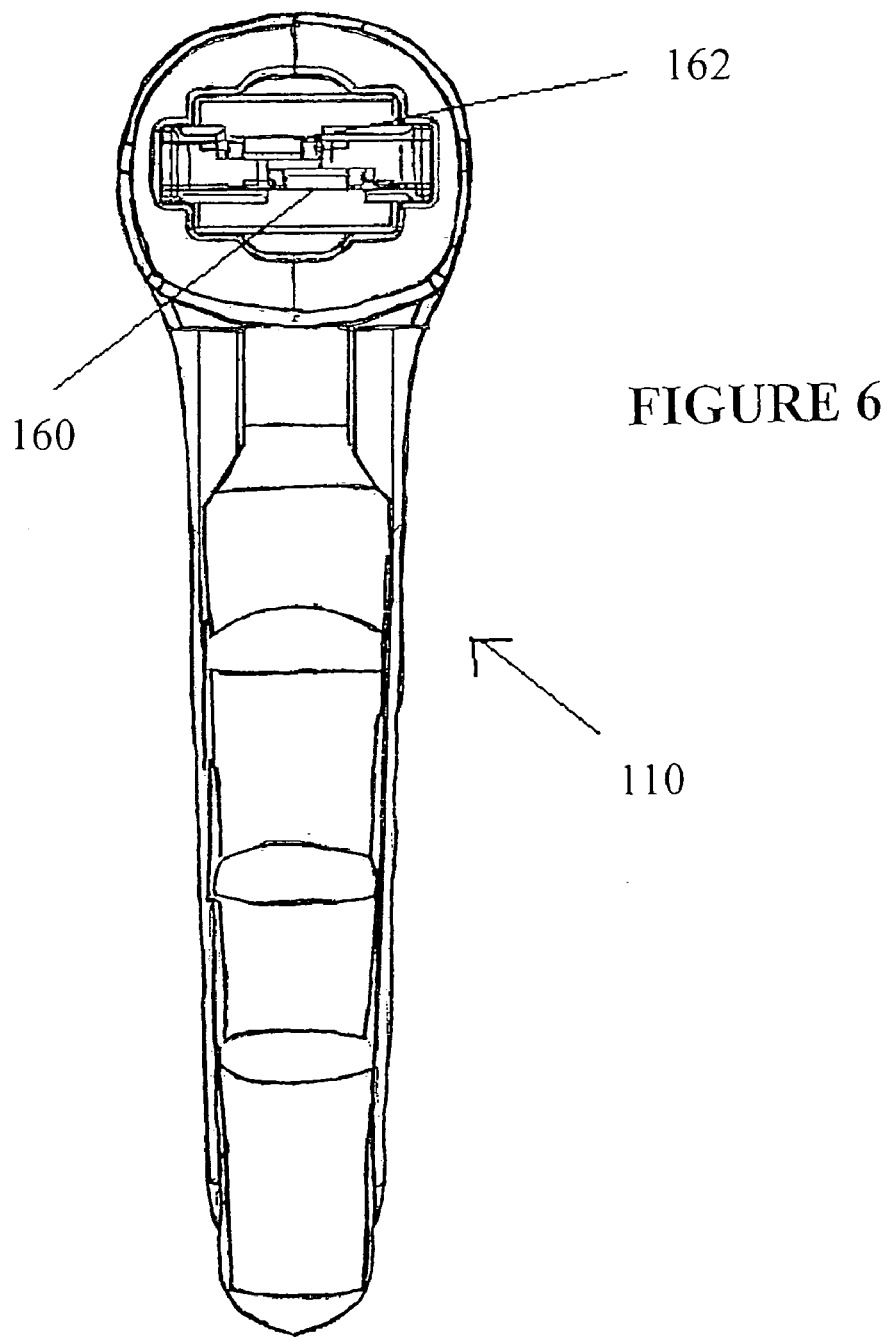
FIG. 6 depicts a front end view of the dual stapler gun.

FIG. 6 depicts a front end view of the dual stapler gun. The holes in which the staples eject from (160, 162) are in a staggered position to ensure when the dual staple disposable surgical gun is used the staples are inserted staggered as shown in FIG. 2.

Figure 7:
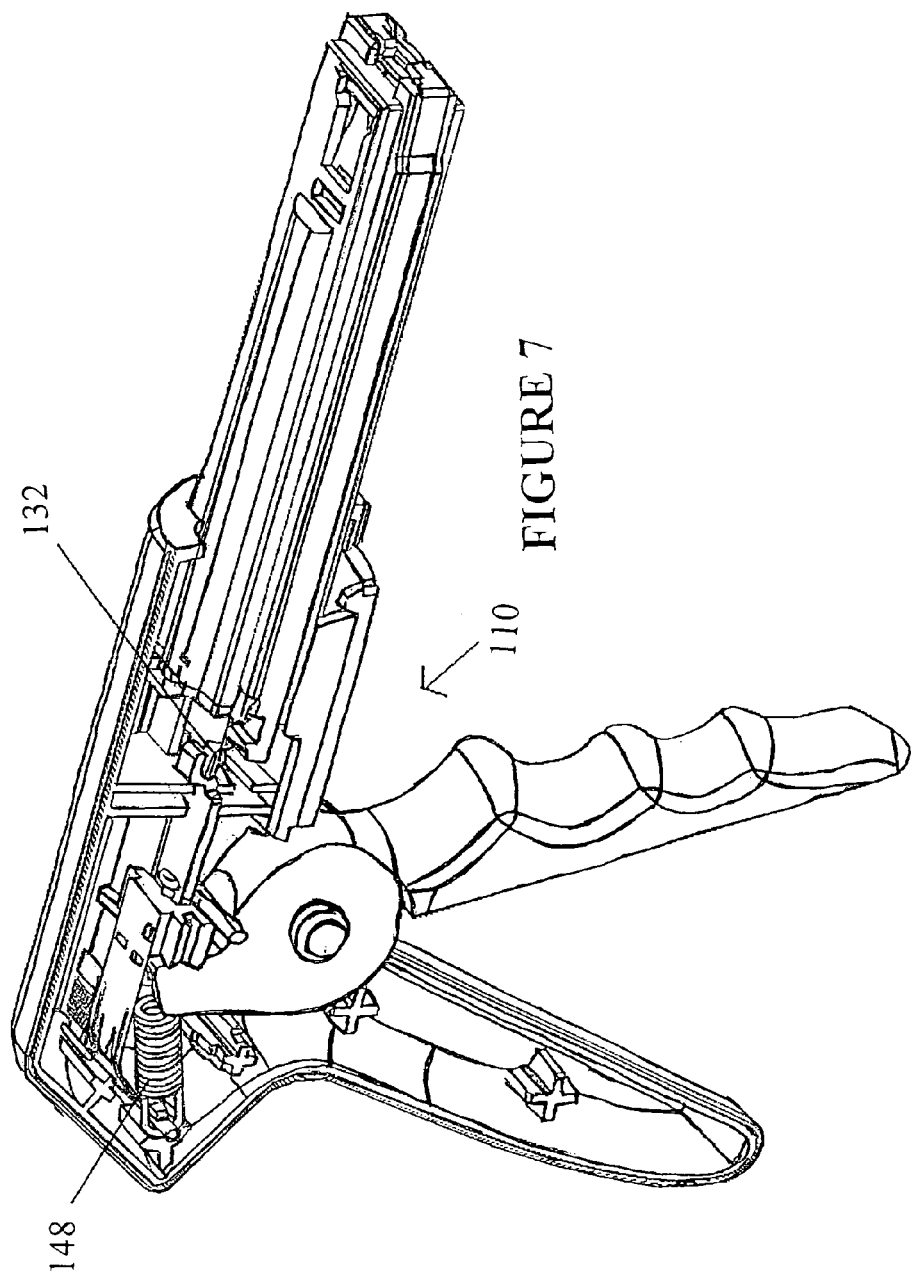
FIG. 7 is an open perspective view of the dual stapler gun.

FIG. 7 is a open perspective view of the dual stapler gun. A translatable driver (132) is used for manually actuating both staple tracks to eject a single pair of staples by hand. A biasing means (148) is used to return the translatable driver from a staple ejecting position to a staple reloading position.

Figure 8:
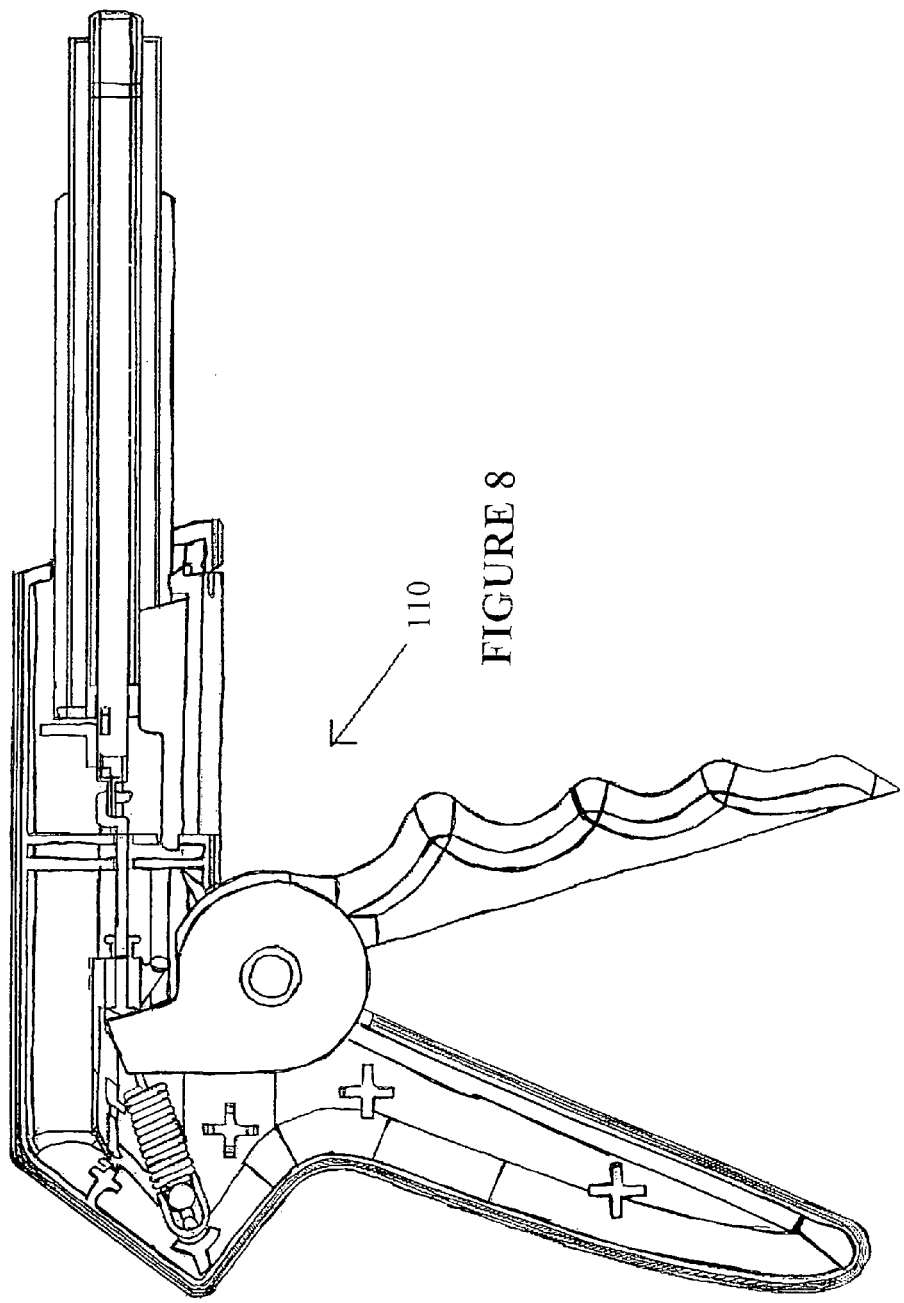
FIG. 8 is an open side view of the dual stapler gun.

FIG. 8 is a open side view of the dual stapler gun.

Figure 9:
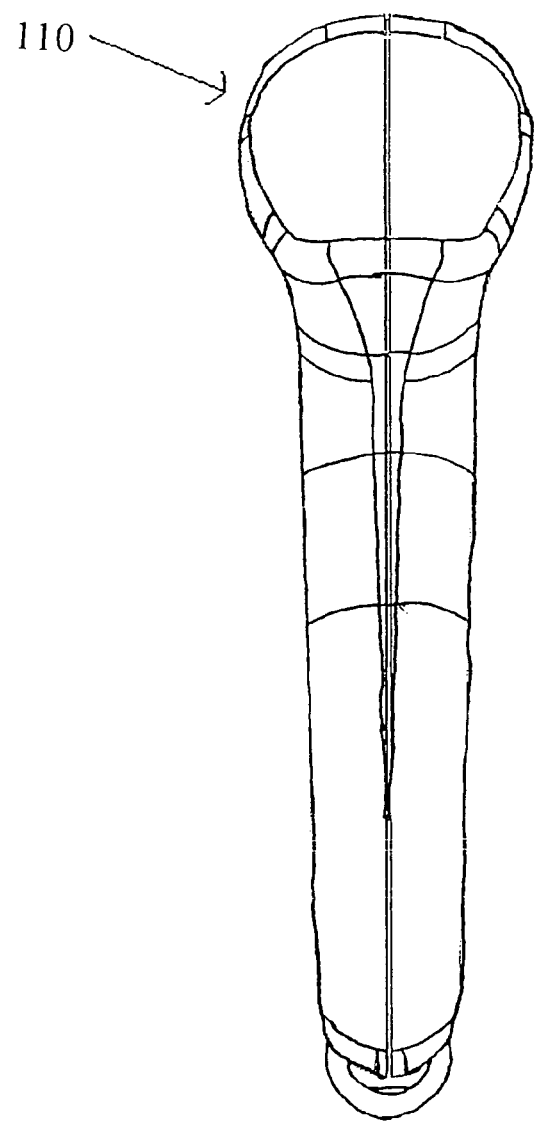
FIG. 9 is a back end view of the dual stapler gun.

FIG. 9 is a back end view of the dual stapler gun.

While the embodiments have been described, it should be understood that within the scope of the appended claims the embodiments might be practiced or carried out in other ways than as specifically described herein.

What is claimed is:

1. A dual staple disposable surgical gun, wherein the gun fires two staples in a staggered formation simultaneously to close an incision with two staggered staples in the skin without the skin overlapping comprising of:

a. a frame structure, adapted to be held by a hand with a grip having a handle;

b. a first staple track and a second staple track each with an advancing blade and a spring mechanism, wherein the first staple track is disposed on top of the second staple track in a staggered relationship, each staple track being adapted for holding staples;

c. a translatable driver for manually actuating both staple tracks to eject a single pair of staples simultaneously by the hand, wherein the pair of staggered staples eject simultaneously for engagement on either side of the incision forming a mattress suture and wherein the first staple engages a first arm close to a first edge of the incision and a second arm a distance from a second edge of the incision and the second staple engages a first arm close to a second edge of the wound and the second arm engages a distance from the first edge of the incision to achieve dual staple mattress suturing; and d. biasing means for returning the translatable driver from a staple ejecting position to a staple reloading position; and the translatable driver having a force transmission member linking together the translatable driver and a connecting end portion engageable with a spring connected to the translatable trigger portion.

2. The dual staple disposable surgical gun of claim 1, wherein the frame structure comprises a first staple track portion inserted into a second holder portion.

3. The dual staple disposable surgical gun of claim 1, wherein the first and second staple tracks each comprise a back and a top and the first and second staple tracks are connected back to back.

4. The dual staple disposable surgical gun of claim 1, wherein the gun uses staples that have a skin piercing projection comprising a point projection, a chiseled projection, a skewed projection, or combinations thereof.

5. The dual staple disposable surgical gun of claim 1, wherein the staple comprises a lightweight, non-rusting alloy of a metal.

6. The dual staple disposable surgical gun of claim 1, wherein the gun is formed from a crystalline polymer, or a metal.

7. The dual staple disposable surgical gun of claim 1, wherein the staples each comprises:
   a. a height ranging from 4 mm to 6 mm;
   b. a length ranging from 2 cm to 3 cm; and
   c. a diameter of the rod ranging from 0.5 mm to 0.8 mm.

8. The dual staple disposable surgical gun of claim 1, wherein the dual stapler fires at least two staples simultaneously each time it is fired.

9. The dual staple disposable surgical gun of claim 8, wherein the two staples are in a staggered in position from each other across the incision after firing.

10. A method for surgically stapling an incision using the simultaneous ejection of offset twin surgical staples comprising the steps of:
    a. inserting surgical staples into a dual staple disposable surgical gun;
    b. wherein the surgical staples each comprises:
       (a) a crown comprising two ends, a first arm, and a second arm attached at each end of the crown, wherein the arms comprise a skin piercing projection, wherein the arms extend from the crown in a direction substantially perpendicular to the crown when the staple is in its initial shape; and
       (b) wherein the dual staple disposable surgical gun comprises a gun that fires two staples simultaneous to close an incision in the skin without the skin overlapping;
    c. placing the dual staple disposable surgical gun over the incision;
    d. activating the stapler by squeezing a grip to simultaneously insert a first staple from a first track and a second staple from a second track into the skin, enabling:
       (a) the first arm of each staple to engage the skin nearest the incision on opposite sides of the incision;
       (b) the crowns of each staple to locate adjacent and parallel to one another; and
       (c) the second arm of each staple to engage the skin away from the incision on opposite sides of the incision; and
    e. using the dual staple disposable surgical gun to bend each arm on the staples forming an inverted G-shape with a gap.

11. The method of claim 10, wherein the step of using the dual staple disposable surgical gun bends each arm to ensure that the first arms intersects the incision.

12. The method of claim 10, wherein the step of using the dual staple disposable surgical gun bends each arm thereby closing the incision in the skin without the skin overlapping.

* * * * *